United States Patent [19]

Olson et al.

[11] Patent Number: 5,404,755

[45] Date of Patent: Apr. 11, 1995

[54] SCANNING APPARATUS AND METHOD FOR NON-DESTRUCTIVE MATERIALS EVALUATION AND MAPPING THROUGH USE OF ACOUSTIC WAVES

[75] Inventors: Larry D. Olson, Lakewood; Dennis A. Sack, Boulder; David Fidelman, Lakewood, all of Colo.

[73] Assignee: Olson Engineering, Inc., Golden, Colo.

[21] Appl. No.: 867,248

[22] Filed: Apr. 10, 1992

[51] Int. Cl.⁶ ............................................. G01N 29/24
[52] U.S. Cl. ..................................... 73/639; 73/12.12; 73/584; 73/649; 73/628; 73/624; 73/641
[58] Field of Search .................. 73/584, 597, 598, 599, 73/600, 618, 620, 624, 632, 633, 639, 635, 12.04, 12.09, 12.12, 12.13, 12.06, 579, 582, 641, 588, 570, 649

[56] References Cited

U.S. PATENT DOCUMENTS

| | | | |
|---|---|---|---|
| 2,836,059 | 5/1958 | Beaujard et al. | 73/620 |
| 3,423,991 | 1/1969 | Collins | 73/639 |
| 3,616,684 | 11/1969 | Nusbickel, Jr. | 73/635 |
| 3,628,375 | 12/1971 | Pagano | 73/639 |
| 3,690,156 | 9/1972 | Robinson | 73/613 |
| 3,732,444 | 5/1973 | Miller | 73/644 |
| 3,937,065 | 2/1976 | Milberger et al. | 73/588 |
| 4,066,993 | 1/1978 | Savit | 367/77 |
| 4,160,386 | 7/1979 | Jackson et al. | 73/625 |
| 4,313,070 | 1/1982 | Fisher | 73/627 |
| 4,457,176 | 7/1984 | Scholz | 73/685 |
| 4,494,410 | 1/1985 | Van Bochove et al. | 73/644 |
| 4,594,895 | 6/1986 | Fujii | 73/599 |
| 4,599,899 | 7/1986 | Jero et al. | 73/584 |
| 4,646,748 | 3/1987 | Fujii et al. | 73/599 |
| 4,668,909 | 5/1987 | Hickernell et al. | 324/56 |
| 4,864,178 | 9/1989 | Bjurling et al. | 73/644 |
| 4,916,535 | 4/1990 | Volodchenko et al. | 358/101 |

FOREIGN PATENT DOCUMENTS

156822 12/1980 Japan ........................ 73/570

Primary Examiner—Hezron E. Williams
Assistant Examiner—Nashmiya Ashraf
Attorney, Agent, or Firm—Earl C. Hancock

[57] ABSTRACT

Columns, walls and other solid structures of concrete, wood, masonry or other materials are non-destructively tested by acoustic signals transmitted from a carriage. The carriage has a frame which is wheel mounted to move over the surface of the test candidate. An internally-mounted piezoelectric crystal roller as an acoustic signal generator or receiver is suspended from the carriage with two degrees of spring freedom to allow accommodation of irregularities in the test candidate surface. The assembly including the piezoelectric crystal roller and its flexible mounting are configured as a replaceable module relative to the carriage frame. The same carriage is useable as an echo type acoustic scanner or, in combination with other devices or carriages, as either an acoustic transmitter or receiver although inclusion of elements to perform both functions within the same carriage is contemplated. The carriage frame can also mount one or more hammer mechanisms to impact the test candidate surface at regular intervals as the carriage moves along the specimen surface. The device is suitable for detecting or generating compression, shear or surface waves in the test specimen.

17 Claims, 8 Drawing Sheets

SCANNING APPARATUS AND METHOD FOR NON-DESTRUCTIVE MATERIALS EVALUATION AND MAPPING THROUGH USE OF ACOUSTIC WAVES

BACKGROUND OF THE INVENTION

1. Field of the Invention

The present invention relates to devices and processes for non-destructively scanning the interior of solid materials with sonic to ultrasonic frequency stress waves. More particularly, the present invention relates to devices and methods for surface monitoring of acoustic vibrations transmitted at least partially through a solid material specimen for interpreting the internal characteristics of that specimen. Further, the present invention relates to devices and methods to provide cost effective, non-destructive scanning and testing of the internal integrity of solid materials including concrete, wood, masonry, stone, steel, etc., with regard to flaws such as cracking, delamination, honeycomb, deterioration and the like. The present invention is a sonic/ultrasonic scanner with compression (P), shear (S), and surface (R or Rayleigh) wave measurement capabilities especially suited for assisting with the sensing and mapping of the internal characteristics of solid structural materials such as structures fabricated of concrete. The present invention has particular utility for non-destructively determining the internal characteristics and quality of structures in place and in their normal environment.

2. Description of the Prior Art

Contemporary non-destructive testing and evaluation of solid structures sometimes employ sonic and supersonic signals introduced into the test specimen to reflect the condition of its interior. Internal defects of the specimen cause slower velocity and lower amplitude signals while severe defects can block the signal entirely. Changes in specimen density and stiffness create acoustic impedances such as is encountered at the boundary wall of the specimen. Reflector depths are calculated based on the echo return time or the resonant frequency of the echo and the concrete wave velocity. Approximate depths of cracks or breaks, voids, soil intrusions, poor quality concrete, honeycomb consolidation problems, and enlargements are determinable by seismic echo and impulse response techniques.

Test data is sometimes obtained by drilling or embedding bore holes parallel to the structure in question, filling those holes with water, and introducing one or more hydrophones into the bore. Wave velocity is typically estimated from ultrasonic pulse velocity measurements sometimes obtained by one or more geophones embedded in the structure.

For direct, through transmission measurement of P and S wave travel in materials with contemporary devices and methods, it is necessary when testing a concrete slab, wall, column or other member, to manually place, on a repetitive basis, both a transmitting and receiving transducer at specific grid locations. An ultrasonic pulse is then introduced via a transmitting transducer, such as a piezoelectric crystal, which converts an electrical pulse into mechanical energy or, in some instances, by striking the surface under test with a small hammer of specific weight. The hammer might have a force transducer associated therewith to measure the force imposed and to signal the occurrence of the impact.

The P and/or S wave produced by either of the above methods travels through the concrete and is sensed by a receiving transducer which might typically also be a piezoelectric crystal. The receiver converts the mechanical wave energy into a corresponding electrical signal. This signal is then collected by an instrument that measures the travel time of the ultrasonic pulses between the source and receiver. An oscilloscope is often used to measure the travel time and record the receiver signal voltage. This procedure for ultrasonic pulse velocity (UPV) measurement is specified for concrete as ASTM C597-83. One of the more significant drawbacks to this method is the time required to manually place, operate, and then relocate the transducers so as to cover an adequate number of points of a grid.

It is known to ultrasonically test slab materials by employing a transducer contained in a roller which is manually movable over the test specimen. U.S. Pat. Nos. 3,628,375 by Pagano and 3,732,444 by Miller are examples. Miller configures the sensing piezoelectric crystal as a cylinder with a protective coating thereover. However, it suffers a serious disadvantage of coupling force variations between the roller and specimen as a direct result of its dependence on manual manipulation to engage the specimen surface. It also provides no indication of the amount of travel over the specimen surface.

Ultrasonic material testing at a fixed station is shown in U.S. Pat. No. 3,423,991 by Collins. It discloses a stationary type ultrasonic testing system for sheets of plywood at a station which uses a pair of cylindrical piezoelectric crystals within rollers. The functionally interchangeable roller transducers are mounted in a fixed frame with spring biasing towards one another. Sheets of plywood are passed between this pair of rollers with one of the fixed rollers actuated as a transmitter and the other operated as a sensor. Collins also discusses adjustability of the angle of incidence of the ultrasonic beam relative to the test specimen as well as operation of a transducer in an echo mode via pulse modulation of the transducer while it is in contact with the specimen.

It is known to interface data processing equipment including displays and computers with ultrasonic testing devices to identify probe locations, produce quality pattern displays, and so forth. Examples are shown in U.S. Pat. Nos. 4,160,386 by Jackson et al, 4,457,176 by Scholz, 4,594,895 by Fujii, 4,599,899 by Jero, 4,646,748 by Fukii, and 4,916,535 by Volodchenko et al. Jackson et al suggest using a multiplicity of sensors in fixed array for making it possible to locate a hand-held inspection probe by detecting signals arriving at the multiplicity of sensors.

Yet another contemporary ultrasonic testing procedure employs a separate hammer mechanism at a first, relatively fixed, location to impact the test specimen while sensing the arrival of the waves therefrom with a sensing transducer at another relatively fixed location. Such devices frequently include a force transducer for providing a feedback signal to the data processing equipment marking the occurrence of a test impact on the specimen by the hammer.

Impact Echo (IE) testing is also a known procedure. An Impact Echo test involves the introduction of an impact and the subsequent monitoring of the surface vibration response in time to identify resonant echoes indicative of the condition of the test member. The IE test involves measurement of the receiver time domain response and subsequent Fast Fourier Transform (FFT) analyses to provide linear displacement spectra of the natural resonant frequency response in structural members to determine their geometry and the presence of flaws in concrete and other solid materials from only one side of the test surface.

It is understood that the IE method was developed for use with P-wave energy at the National Institute of Standards and Technology by Dr. Nicholas Carino and Dr. Mary Sansalone in the 1980's for evaluation of slabs and other structural concrete members. It is further understood the development was continued by Dr. Sansalone at Cornell University for a point-specific, non-moving IE test system.

A significant disadvantage of the prior art IE systems is the time and inconvenience in setting up the sensors so as to obtain reliable data. That is, none of the known prior art devices are suitable for rapid and reliable production of substantial test data from specimens while in its normal environment such as concrete walls and columns of a structure. These and other disadvantages are overcome by the present invention as is described in greater detail below.

It is believed Spectral-Analysis-of-Surface-Wave (SASW) measurements were developed by Dr. Kenneth H. Stokoe, II. The current state of the art in SASW measurement involves coupling two transducers to the test medium at a given spacing and then impacting one, or both, ends of the receiver line at approximately the same distance away from the closest receiver as the receiver spacing. The SASW test involves measuring the surface wave propagation velocity between the receivers as a function of wavelength.

DISCLOSURE OF THE INVENTION

An ultrasonic echo scanner in accordance with this invention has several important innovations including moving IE testing to provide nearly continuous measurements along a test path. Measurement of the impact force provides input relative to both linear spectral displacement and displacement/force transfer function amplitudes versus frequency especially for P-waves. The incorporation of an automated, electrically actuated, solenoid driven impactor source, and the ability to dynamically perform both P and S-wave IE measurements (possibly as linear spectra for S-wave only) are further features of this invention. Ultrasonic scanners in accordance with this invention by virtue of its capabilities for P and S-wave sensitivity can also measure the perpendicular and right-angle parallel components of surface (R) wave travel in a test member while moving by use of the IE source mechanisms and a multiple receiver transducer configuration. For a flat, horizontal surface, the scanner can thus measure the vertical and horizontal components of an induced surface wave. The ultrasonic surface wave scanner thus is useful to perform SASW measurements with the use of two or more receiving transducers to provide the phase data on the vertical and horizontal components of a surface wave traveling in a flat, horizontal medium. In contrast to the prior art, the present invention provides for moving, nearly continuous surface wave measurements with potentially either fixed or variable receiver spacings in the mechanism.

By utilizing the scanner of this invention, it is no longer necessary to manually place individual transducers at specific grid locations. The scanner device, as its name implies, can scan or test a given member by simply rolling along the surface of that member collecting data on a continuous basis. This data is then stored in a computer for analysis upon completion of the scan. Scanning is, therefore, a much faster, more efficient and cost effective method of collecting data.

This is accomplished by measuring the time delay, frequency and phase of sonic energy passing through (or reflected as an echo from within) the section of concrete or other material under test. By careful analysis of this time and energy data which is digitally recorded on an oscilloscope and computer supported by dedicated software, an accurate determination of the internal quality of the material under test is possible.

The carriage transducer apparatus and method of this invention in one form includes the capability of introducing acoustic waves to a material and/or receiving acoustic waves generated from itself (in IE mode) or from another source. Carriage assemblies of this invention can take the form of modules having interchangeable utility for either transmit or receive purposes or both. A process for utilizing the carriage assemblies is to move one of the carriages along a first side of the material that requires testing, and to concurrently move the other along the opposite side of that material. Power is applied to a piezoelectric crystal contained in a roller assembly in one of the carriages while the response received, such as at another crystal in the opposite carriage, is monitored.

The carriage assemblies are well suited for coupling input into a computer from both devices. The computer can log the actual rolling movement of both carriages and determine the angle between those devices through the material under test. That is, by measuring the amount of travel of each carriage, the computer can determine the angle of travel of the sonic wave through the material and pinpoint the location of anomalies encountered by the wave within the structure.

Thus, it is possible to interchangeably utilize identical transmitter/transponder carriages. A typical carriage is implemented with rollers or wheels at each corner and a roller drum formed from, or with, a piezoelectric crystal as an element thereof. This roller drum is contained by an assembly that is spring biased towards the surface over which the carriage moves. This maintains intimate contact between the crystal drum surface and the surface of the materials under test. Electrical connections to the carriage allow it to receive power from an actuating device (a computer, for instance) as well as for providing responsive signals as received.

Several variations are contemplated for the carriage configuration. For instance, a single carriage with both a powered output roller and a receiving roller each with its own piezoelectric crystal is possible. With this configuration, one crystal is actuated to direct pulses of audio sound into the materials for testing, and the other roller is employed to detect the presence of reflected echo signals from within the materials. The echoes are from either flaws within the materials or from the far surface, as well as from intervening surfaces (as in laminated structures) within the materials under test. A particularly useful application of the device is for determining the integrity of concrete columns, steel or metal plates, or the like, while they are in place in their normal operating environment.

An alternative to the foregoing is to replace one crystal with a mechanical impactor or with an electrically actuated solenoid driven hammer/impactor assembly. The assembly imparts known amounts of acoustic energy into the test member, and the echoes are received by the remaining crystal within a single carriage unit.

Yet another variation is to employ a single transmitting crystal in one location, such as the center of a carriage assembly, with a plurality of receiving crystal rollers arrayed around it so that a pattern of echo pulses is developed as the carriage moves over the surface of the material under test. The advantage of using a single carriage with echo signal reception interpretation is that this avoids the necessity for interpreting the angle of displacement between two carriages as where identical carriages are employed in a sandwich relation on either side of the materials under test.

Still another alternative is to employ at least two receiving crystals and a mechanically or electrically operated hammer all retained in fixed relation along an alignment on one face of a test member. Preferably, the crystal elements and hammer mechanism are maintained in an evenly-spaced relationship with the hammer fixed at one end of the line of the units. Generating sonic pulses with the hammer and measuring the phase change between the two receivers allows the implementation of the SASW test method. This method is one which allows the measurement of shear wave velocity of a material as compared to depth, and thus allows visualization of the internal structure of a test member.

Thus, the apparatus and methods of this invention are useful for transporting acoustical testing mechanisms across the surface of a solid specimen for analyzing the quality of the interior of that specimen. An assembly acoustically communicates either as a transmitter or receiver relative to the specimen. A frame is configured for movement over the surface of the specimen with a relatively constant spacing therefrom. The acoustic assembly is attached to the frame for engaging the specimen surface as the frame is motivated over the specimen surface.

Another feature of this invention is in the retaining of the acoustic assembly in constant engagement with the specimen surface despite irregularities therein. A flat spring and a pivotable link arranged between the assembly and the frame can provide the retention function. With the flat spring oriented generally parallel to the specimen surface, a parallelogram is formed perpendicular to the specimen surface in conjunction with the link. The acoustically-communicating assembly can take the form of a roller with an acoustically-communicating element retained as part of, or within, the roller.

The method of this invention employs an acoustically-communicative element for analyzing the quality of the interior of a solid specimen. An acoustic signal is introduced into the specimen through the surface thereof. The acoustically-communicative element is then moved over the surface of the specimen with a relatively constant spacing therefrom. The acoustic signals introduced to the specimen are detected at the surface of the specimen after those signals have passed through at least a portion of the interior of the specimen.

Piezoelectric crystals are well suited to provide the acoustically communicative element and introduction of electrical signals can actuate the crystal for generating the acoustic signals. Alternatively, the piezoelectric crystal operating as the acoustically-communicative element can perform a detection function for sensing the presence of acoustic signals at the crystal.

The acoustically-communicative element can include a second piezoelectric crystal which is electrically actuated for generating the acoustic signal while detecting the amount of movement of the crystal over the surface of the specimen and producing a signal indicative of the results of movement detection.

Those having normal skill in the art will recognize the foregoing and other objects, features, advantages and applications of the present invention from the following more detailed description of the preferred embodiments, as illustrated in the accompanying drawings.

DETAILED DESCRIPTION OF THE PREFERRED EMBODIMENTS

Figure 1:
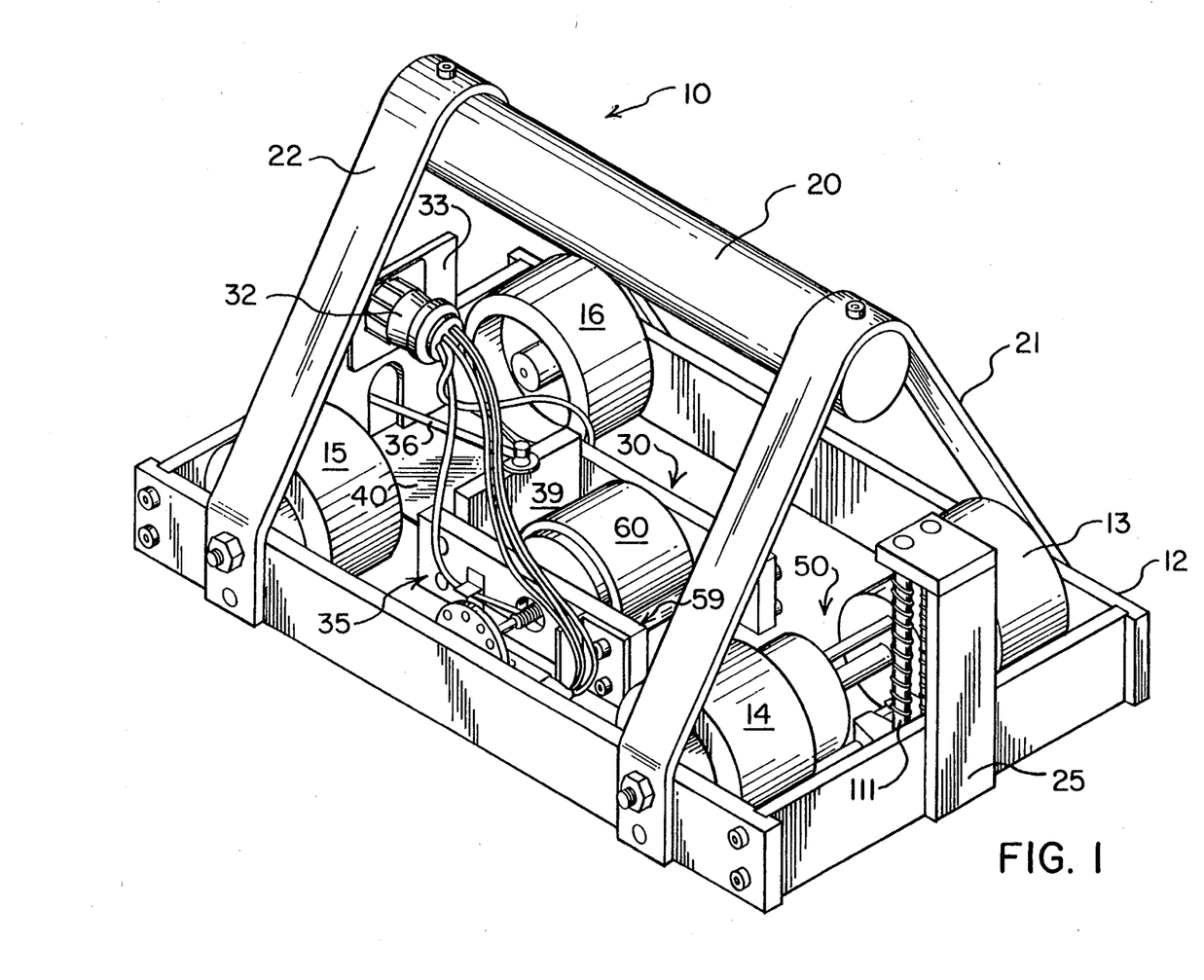
FIG. 1 is an isometric view of a tester embodiment of this invention showing the interrelationships of some of the components in a carriage assembly.

FIG. 1 shows a preferred embodiment of a scanner unit 10 in accordance with the present invention, with certain protective covers omitted for clarity. A generally rectangular main frame 12 has four wheels 13 through 16 pivotably attached thereto, as shown, thereby allowing it to roll smoothly over a test surface. A handle 20 is attached to the main frame 12 by brackets 21 and 22 to permit the user to manually move the carriage.

The exemplary unit 10 as shown includes two assemblies in the form of impactor mechanism 25 attached to frame 12 at one end, and transducer assembly 30 attached as a module to the other end of frame 12. Either of these assemblies 25 and 30 are removable and/or replaceable depending upon the function the user intends for unit 10.

Transducer assembly 30 includes a multi-pin connector 32 for coupling to a suitable cable for interfacing with a data link to a computer or other data handling equipment. Connector 32 is secured to vertical plate 33 of assembly 30. The transducer assembly 30 is secured to the main frame 12 by beam 34 to which plate 33 is likewise attached, as best seen in FIGS. 2 and 3.

Figure 2:
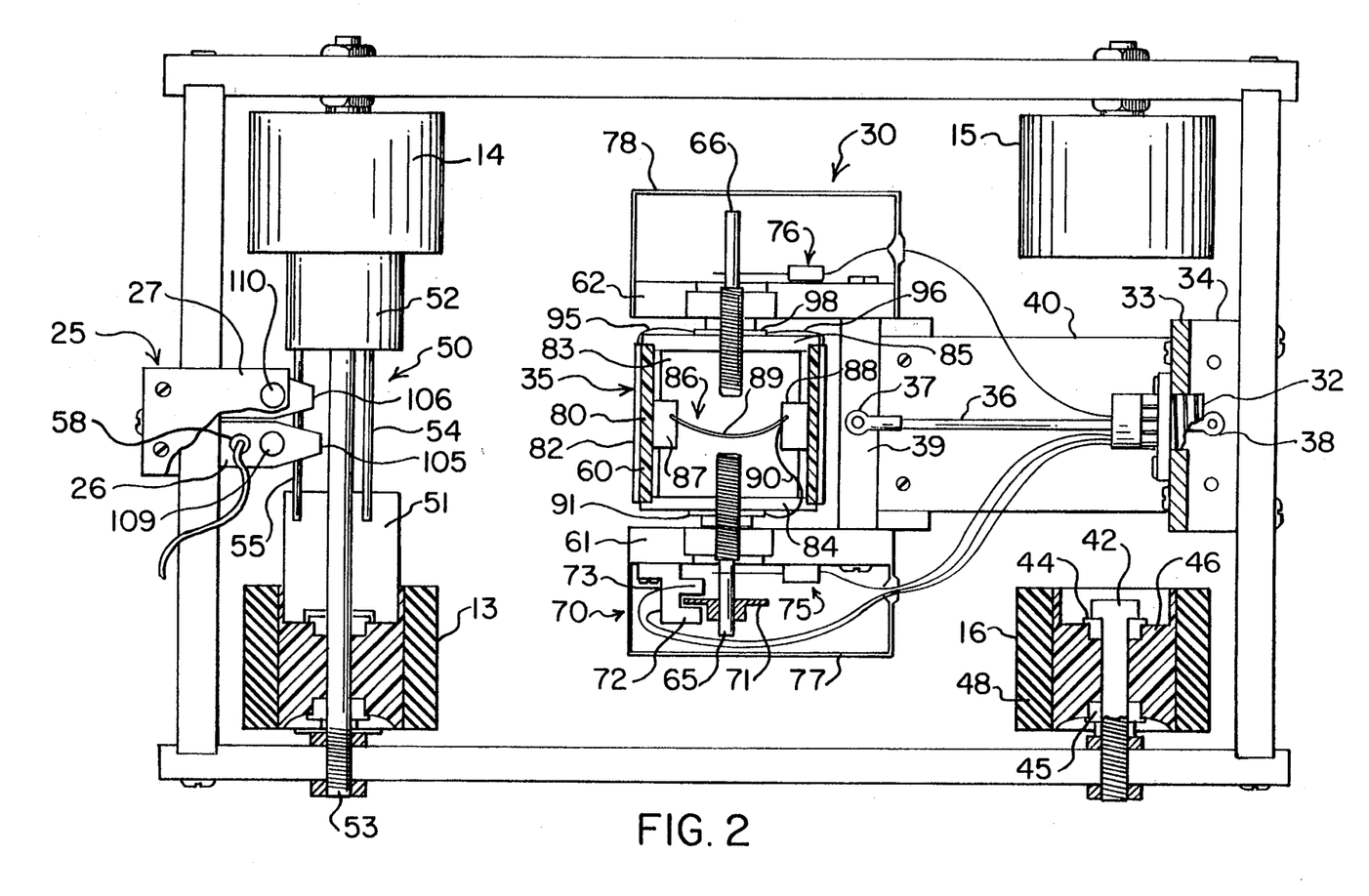
FIG. 2 is a partially broken and partially sectioned top view of the FIG. 1 embodiment showing the transducer assembly with protective covers.
Figure 3:
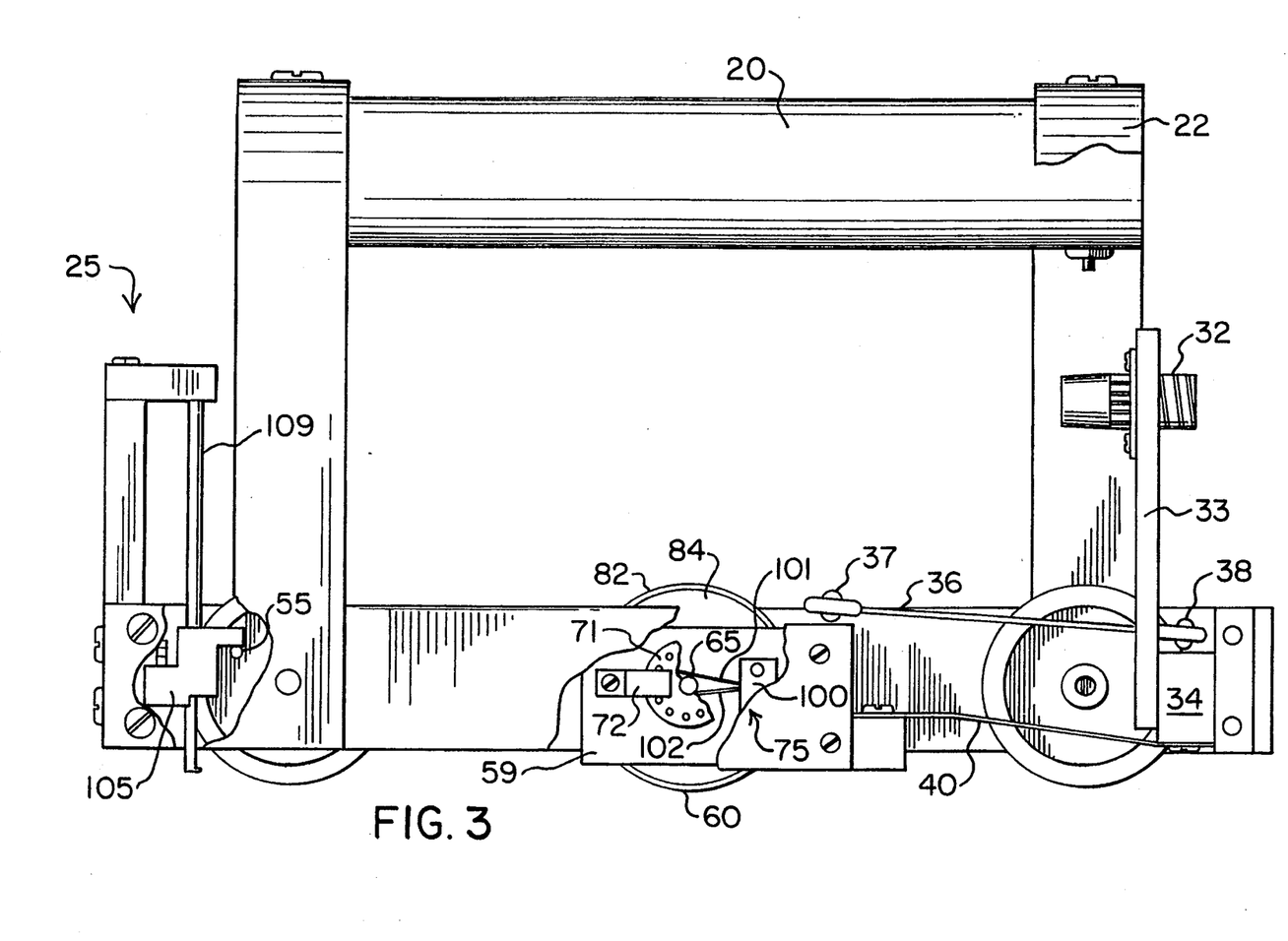
FIG. 3 is a side view of the FIG. 2 device which is depicted partially broken and sectioned to show the details of the hammer, flat spring and link, and the optical coupler/tachometer subassemblies.

A transducer mounting subassembly 35 forms part of assembly 30, as is illustrated in partially broken and sectioned views of FIGS. 2 and 3. The frame members of subassembly 35 are flexibly attached to beam 34 by a link 36 which is pivotably attached on one end to plate 39 by a ball joint 37 and on the other end to beam 34 by ball joint 38. A flat spring 40 completes the attachment of subassembly 35 to beam 34 in a parallelogram configuration.

FIG. 2 shows the wheels 13 through 16 and the transducer assembly 30 in more detail. Wheels 13 and 16 are shown in sectioned detail by way of example. Wheel 16 is mounted to axle 42 by two ball bearings 44 and 45 between axle 42 and wheel hub 46. Tire 48 surrounds the inner hub 46. Wheel 15 is constructed the same as wheel 16. Further, wheels 13 and 14 are constructed similarly, but also have hammer actuator 50 positioned therebetween.

Actuator 50 includes drums 51 and 52 as extensions from the center hubs of wheels 13 and 14, respectively. Drums 51 and 52 contain pins 54, 55, and 56 (the latter of which is not shown in the drawings) which are used to raise and drop hammer elements of impactor assembly 25 as described below. Actuation of the impactors is sensed by force detector 58 to provide a data processing feedback signal signifying the impact event. The output of detector 58 is coupled through a connector separate from connector 32 in the embodiment shown although it is acceptable to combine it with connector 32 if transducer assembly 30 is not fabricated as a replaceable unit. Drums 51 and 52 are attached to the inner hubs of wheels 13 and 14 so that they freely rotate as a unit with wheels 13 and 14 around axle 53.

The transducer roller 60 of assembly 30 is mounted on a U-shaped frame 59 comprised of end plate 39 and side members 61 and 62. Frame 59 is attached to the main frame 12 only by flat spring 40 and link 36. Spring 40 and link 36 form a parallelogram with beam 34 and plate 39, so that transducer roller 60 can float with respect to the main frame 12, but must remain horizontally parallel to it. That is, roller 60 is allowed to flex vertically and laterally relative to the plane of main frame 12 as the carriage 10 moves over any irregularities in the surface of the specimen under test. However, it cannot change its position relative to the direction of movement of carriage 10.

Link 36 is attached to the beam 34 and the frame 59 plate 39 by ball pivots 37 and 38. Ball joint assemblies 37 and 38 are formed by upwardly extending stubs from both plate 39 and beam 34 with a ball on the upper end of each of those stubs to fit within a partially surrounding socket on respective ends of link 36. These couplings, in conjunction with the width of flat plate spring 40, permit the vertical and lateral movement of roller 60 while retaining a fixed relationship relative to the direction of movement of carriage 10.

The roller assembly 35 includes axles 65 and 66, a tachometer 70, brush assemblies 75 and 76, dust covers 77 and 78, and U-frame 59. The elements of tachometer 70 include optical disk 71, a light source in arm 72 and a light detector in arm 73 electrically connected into plug 32. Note that it is acceptable to mount the tachometer 70 in association with one of the wheels 13–16 or on its own separate roller.

Figure 4:
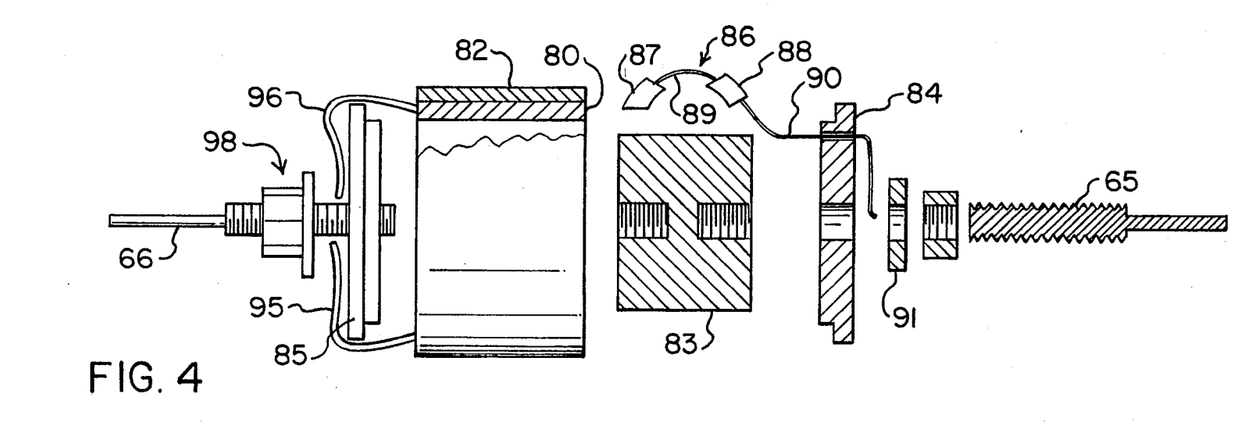
FIG. 4 is an exploded view of a typical roller mounting of a piezoelectric crystal with some components partially broken and/or in section.

The roller transducer 60 is shown in exploded view in FIG. 4. A cylindrical piezoelectric crystal element 80 with a polyurethane coating 82 slips over inner plastic spool formed by cylinder 83 and end washers 84 and 85 to form the core. An inner electrode connector 86 is formed by electrodes 87 and 88 which are fabricated of arched conductive spring material which, with wire 89, are electrically connected to axle 65 by lead 90 which passes through washer 84 and is secured under nut and washer 91. Note that, for purposes of clarity in illustration, inner connectors 86 are shown slightly turned from their normal position over the peripheral surface of spool 83 which perhaps is better understood from viewing FIG. 2.

The outer and inner peripheral surfaces of crystal 80 are actually electrodes sandwiched over the piezoelectric material. These outer and inner electrodes have connector extensions 95 and 96 which are electrically connected to axle 66 by means of nut and washer 98. The inner spool and washers are all made of electrically non-conductive material so that axles 65 and 66 are electrically insulated from one other.

In operation, the present invention allows the operator to grasp the handle 20 and easily roll the device 10 along the surface of the materials under test. Within the central area of the frame 12 is located an interchangeable module 30 consisting primarily of a cylindrical piezoelectric crystal 80 coated with a polyurethane compound 82 of specific durometer. The coated crystal assembly is mounted in a small frame 59 which allows it to rotate similar to a wheel when in contact with and moving along a flat surface.

The frame 59 supporting the crystal 80 is attached to the aluminum main frame 12, described earlier, by means of flat spring 40 and link system 36 designed to keep the rolling crystal 80 under spring pressure and in positive contact with the surface under test when the four wheels 13–16 of main frame 12 are in contact with said surface. The flat spring 40, while primarily for the purpose of holding the outer surface 82 surrounding crystal 80 in contact with the surface under test, is also designed to allow the crystal to follow uneven surfaces during the scanning operation.

The coated crystal 80 is polarized in such a manner so as to expand in diameter, length, or both, when pulsed with a specific frequency and/or level of electrical energy. This allows for the introduction of either, or both, compression and shear wave energy. The electrical energy necessary to activate crystal 80 is routed through a system of brush assemblies 75 and 76. These assemblies are substantially the same with the configuration of assembly 75 best seen in FIG. 3. The electrical leads from connector 32 are coupled to spring brushes at blocks which are secured to side walls 61 and 62, respectively. For example, springs 101 and 102 of assembly 75 in FIG. 3 are biased into rotating contact against axle 65. This design allows the crystal 80 in roller 60 to roll without restriction.

While not shown, it is possible to suspend a brush or cleaner blade from the crystal roller 80 mounting frame so as to engage the outer surface of the roller on the downstream side (i.e., in proximity to where the roller leaves the specimen surface). This would remove any dirt, stones or other debris from the roller surface to minimize interference with acoustic coupling into the specimen when the thus brushed area is again in contact with the specimen surface. It is also possible to include a lead brush or cleaner blade to push aside debris from the specimen surface ahead of the roller if desired.

Another technique to enhance the acoustic coupling from the roller into the specimen is to inject an ultrasonic compliant, water, or an appropriate fluid agent, along the forward nip of the roller as it engages the specimen surface to enhance acoustic signal interchanges between the roller and the specimen. For instance, the carriage could mount a container of such fluid with means for releasing a spray as the carriage moves. Other configurations are acceptable such as attachment of the container to the belt or backpack of the user with a manual operation thereof possibly with pressurization of the container.

By constructing roller assembly 30 as a removable module, it becomes possible to employ a wide variety of crystals with different resonant frequencies and energy levels which are easily field mounted in the main frame 12 for the purpose of adapting to numerous field conditions. In addition to the main frame 12 capability of supporting many different rolling crystals as both transmitters and receivers, a modular impactor 25, with either one or two heads, are attachable on frame 12 even without the crystal module 30 to allow the operator to perform impact echo, as well as direct impact and shear sonic velocity testing. Thus the carriage of the present invention is useful for introducing periodic impacts at spaced locations along a specimen with fixed sensors, fixed impactors with moving sensors, or both the impactors and the sensors moving or movable.

Hammer assembly 25 is also modular in design and, as shown, includes dual hammer elements 26 and 27 set to give two impacts in quick succession with a specific distance between each pair. If desired, it is possible to configure hammer elements 26 and 27 so that one of them is selectively prevented from impacting (as by a releasable retainer pin) or to function concurrently to generate unitary continuous impacts of equal spacing. The retaining bracket associated with either or both of hammer elements 26 and 27 can carry a force transducer, like detector 58, which is useful to measure the level of energy applied to the test area as well as trigger the computer to begin the timing cycle.

The main assembly, or chassis 12, upon which all other major subassemblies are mounted, is fabricated from four separate but similar pieces of aluminum flat stock, two short and two long, fastened end to face so as to form a rectangular frame. The four wheel assemblies 13–16 are identical in construction and size consisting of a die cast spoked wheel made of plastic with a foam rubber tire (e.g., 48) permanently mounted about the outer circumference. Each wheel contains two ball bearings (note 44 and 45) located at the center hub (46) to allow the wheel to rotate freely about the axle. The axles are located within frame 12 in such a way as to position one wheel at each inside corner thereby allowing the frame assembly to freely roll across any surface in a given direction. Of course, inclusion of a drive motor to power one or more of the wheels 13–16 is possible as is remote control of such a drive.

The U-frame assembly 59 is the primary piezoelectric module support structure to which the bearings which support rolling transducer 35, electrical brush contacts 75 and 76, flat spring 40 and link 36, optical interrupter 70 and dust covers 77 and 78 are mounted. It is fabricated from three separate pieces; the two side frames 61 and 62 of plastic and the back plate 39 of aluminum. The purpose of the plastic sideframes is to provide an insulating surface to which the electrical brushes are directly mounted.

The rolling transducer module 30 is useable as either a transmitter or receiver. It consists of a cylindrical piezoelectric crystal element 80 with a coat 82 of a polyurethane compound of specified durometer. The purpose of coating 82 is to provide a good sonic conductor between crystal 80 and the test surface as well as for protection of the element. The coated element 80, having two short flat brass wires 95 and 96 connected to the outer electrode, is placed over a plastic drum 83 and is held in position by two plastic end caps 84 and 85. A phosphor bronze contact 86 is positioned between the plastic drum 83 and inner surface of the cylindrical element 80 thereby making contact with the inner electrode.

Protruding axially from the center of each end of the plastic drum 83 are identical brass axle halves 65 and 66, partially threaded and electrically isolated from one another, onto which a nut is placed to retain the element end caps. Under these same retainer nuts are captured the lead wires 95 and 96 from the crystal electrodes thereby making each axle half 65 and 66 electrically common with its respective electrode. This element and drum assembly is located between the two plastic sideframes 61 and 62 of the module frame assembly 59, and is allowed to rotate freely about its axis on ball bearings. These ball bearings are located within the sideframes 61 and 62 through which axles 65 and 66 pass.

Two identical brush assemblies 75 and 76 are each fabricated from a small brass block into which four phosphor bronze wires (e.g., 101 and 102) are placed and soldered so as to protrude from the edge of a block (100). To each plastic sideframe 61 and 62, a respective brush block assembly 75 and 76 is mounted, allowing the phosphor bronze wires to maintain a spring contact with its respective axle half. This system provides an electrical path to both electrodes of the rolling element 35 without hindering its ability to rotate freely.

The purpose of the interrupter 70 is to provide a means by which the distance that the scanner unit 10 has traveled is measured and correlated with test data gathered during the scan to provide accurate location information. A small disk 71, having twelve equally-spaced holes drilled in a circular pattern, is attached to the end of one axle half so as to rotate in harmony with the element. A small optical coupler consisting of an infrared LED in arm 72 facing a phototransistor in arm 73 is mounted on the sideframe 61 to allow the hole pattern of disk 71 to pass between the LED and phototransistor causing the phototransistor to turn on and off during rotation of the element. The number of interruptions, or on and off cycles of the phototransistor, is directly proportional to the distance traveled which is readily calculated by the computer.

Flat spring 40 is made of a single or multiple pieces of thin phosphor bronze material, the purpose of which is to provide constant downward pressure on the rolling crystal element 80 during the scanning operation, while also allowing roller element 35 to follow uneven surfaces. One end of flat spring 40 is rigidly mounted to main frame 12 via beam 34, while the other is secured to the module frame 59. A link 36, approximately the same length as flat spring 40 and having a ball socket at each end, is mounted slightly above and parallel to spring 40. This link and spring combination forms a parallelogram upon which the module frame pivots thereby keeping the module aligned with the direction of carriage movement, but parallel to the test specimen surface at all times.

Hammer elements 26 and 27 employ respective small metal blocks 105 and 106, free to move in the vertical direction, sliding upon and guided by a rod 109 and 110 rigidly mounted to main frame 12. In its rest state (down position), the hammer tip may contact the surface upon which the scanner is placed. When the scanner is rolled in the forward direction during testing, the hammer is lifted by one of three pins 54, 55 and 56 projecting from a pair of drums 51 and 52 located between and attached to the rear wheels 13 and 14. When the hammer is lifted to a predetermined height, the pin moves out from under the hammer allowing it to drop, imparting wave energy to the mass under test.

As is evident in FIG. 2, the outward extension of the upper portion of hammer blocks 105 and 106 determines which of them is released first by an engaging pin 54, 55 or 56. As shown in FIG. 2, the hammer element of block 106 is released before the hammer for block 105. These hammer blows are continued at precise time and/or distance intervals on a repetitive basis as long as the scanner is moving in the forward direction. The downward motion of the hammer is assisted by a coil spring (note spring 111 in FIG. 1) placed around the guide shafts 109 and 110 thereby allowing use of the hammer module in any orientation.

The hammer module can also provide for the use of two hammers mounted side by side, as shown, to provide two impacts in quick succession with a measured distance therebetween. This is accomplished by having the horizontal finger on hammer 105 slightly longer than that of hammer 106 (note FIG. 2). This causes the actuator pin 54, 55 or 56 to slip out and drop hammer 105 a predetermined time after hammer 106 is dropped. Inclusion of conventional slip springs, or one-way spring clutches between wheels 13 and 14 and the actuator drums 51 and 52, can prevent damage to elements associated with the hammers when the carriage is rolled oppositely from the normal actuation direction of the unit. Note that the user can manually operate the hammer, or hammers, to produce repetitive impacts at the same location without moving the carriage if desired.

The design of either or both hammers can include fittings for a force transducer (58) which provides a precise measurement of impact energy along with a trigger pulse to start the timing cycle. Further, while the actuator mechanism 50 is relatively simple and well suited for field use, it is possible to employ solenoids which are electrically actuated to drive an impactor hammer against the specimen surface under control of a remote signal generator communicating with unit 10. An alternative is to enable the solenoid with pulses from a device, such as the optical interrupter or tachometer 70 type of mechanism. Solenoid actuation of a hammer element has the advantage of permitting repetitive impacts of the hammer element at the same location without moving the carriage.

One device constructed in accordance with this invention employed an oblong aluminum frame 12 approximately five-by-eight-inches in outer dimension and one-inch high. Within this frame, wheels 13-16 were approximately two-inches in diameter and located within the frame, one within each corner. Handle 20 was a cylinder four-to-six-inches in length and one-inch in diameter, supported by inverted "V" brackets 21 and 22 of flat aluminum stock attached to frame 12 so as to locate handle 20 four or five-inches above frame 12 and along the center line. This allows comfortable grasping by the user to control positioning and movement of scanner/tester 10.

Figure 5:
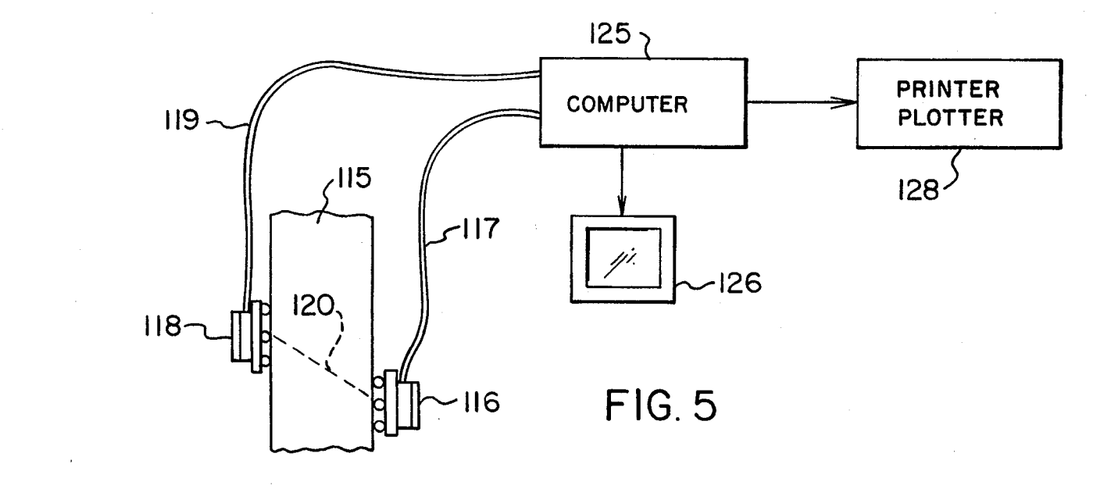
FIG. 5 is a block diagram of the interconnections for electronic data processing elements with dual acoustic sensors in a typical field environment.

A schematic block diagram of the electrical interfacing between dual scanners each similar to unit 10, and data processing elements in a typical scanning or testing operation of a solid concrete column 115, is presented by FIG. 5. That is, scanners 116 and 118 are constructed substantially in accordance with the unit 10 configuration. Cables 117 and 119 provide electrical signal interchanging for respective scanners with computer 125. Various other devices and techniques are available for establishing this communication link, such as by use of optical cable links, by incorporating modulator/demodulator circuits on the carriage for radio frequency signal communications, and so forth.

In the example of FIG. 5, it is assumed unit 116 sends an output acoustic signal beam 120 which the unit 118 receives. The computer 125 is presumed to have introduced an actuating signal to unit 116, although it could passively monitor pulses from hammer impact detectors 58 associated with unit 116. If the units 116 and 118 were originally positioned at the bottom of column 115 so that they are nearly directly across from one another, computer 125 can determine the thickness of column 125 if desired.

As units 116 and 118 are manually moved upwardly along the opposite sides of column 115, they may become displaced from one another so that the acoustic beam 120 is following a slanted path between the units. However, with a tachometer 70 or similarly functioning device, computer 125 can track the relative position between units 116 and 118 so as to determine the slope of beam 120 and produce an accurate representation of the location of anomalies within the interior of column 115. This is especially useful in circumstances where a solid wall is under scan and it is difficult to coordinate and synchronize the movements of scanners on both sides thereof.

While relatively continuous movement of carriages 116 and 118 over the specimen surface allows acquisition of substantial data on the interior of specimen 115, there are advantages to planned movements of a less regular nature. For instance, the user could stagger movement of carriages 116 and 118 and/or alternate utilization of them as transmitters and receivers. This can permit the user to record data that represents a three dimensional mapping of an anomaly, flaw, laminar layer, imbedded object, or the like which is totally contained within the interior of specimen 115.

Therefore, computer 125 can effectively produce a map of the interior of column 115 and can further transfer the results to any of a variety of utilization devices. For instance, it can reproduce the scanning results dynamically to the users on peripheral devices such as display 126 and/or as a permanent copy on a printer or plotter 128.

A similar result is possible using a single scanner in echo mode. That is, computer 125 could enable the crystal of unit 116 with a pulse and then record any reflected echo signal, as from the inside of the far wall of column 115, or from any discontinuity or surface between the outer surfaces of column 115. This type of operation is described in greater detail in conjunction with FIG. 7 below.

Alternatively, computer 125 can enable a solenoid in unit 116 to drive a hammer against the specimen surface, or can rely upon the mechanical hammer actuator of the FIGS. 1-3 embodiment to provide the impacting with a feedback from the force detector on the hammer block. A solenoid implementation is described subsequently for FIGS. 9 and 10.

The system configuration illustrated in FIG. 5 is particularly well suited for field implementation and use. The output of computer 125 is readily adaptable to connection to other data processing equipments as by cables, communication links, etc. Note that it is conceivable to incorporate computer 125, display 126 and/or the printer 128 directly on the frame of a scanner. However, it is generally preferred with contemporary technology to configure the elements separately as shown so as to minimize the size and weight of the portable units.

Figures 6, 10:
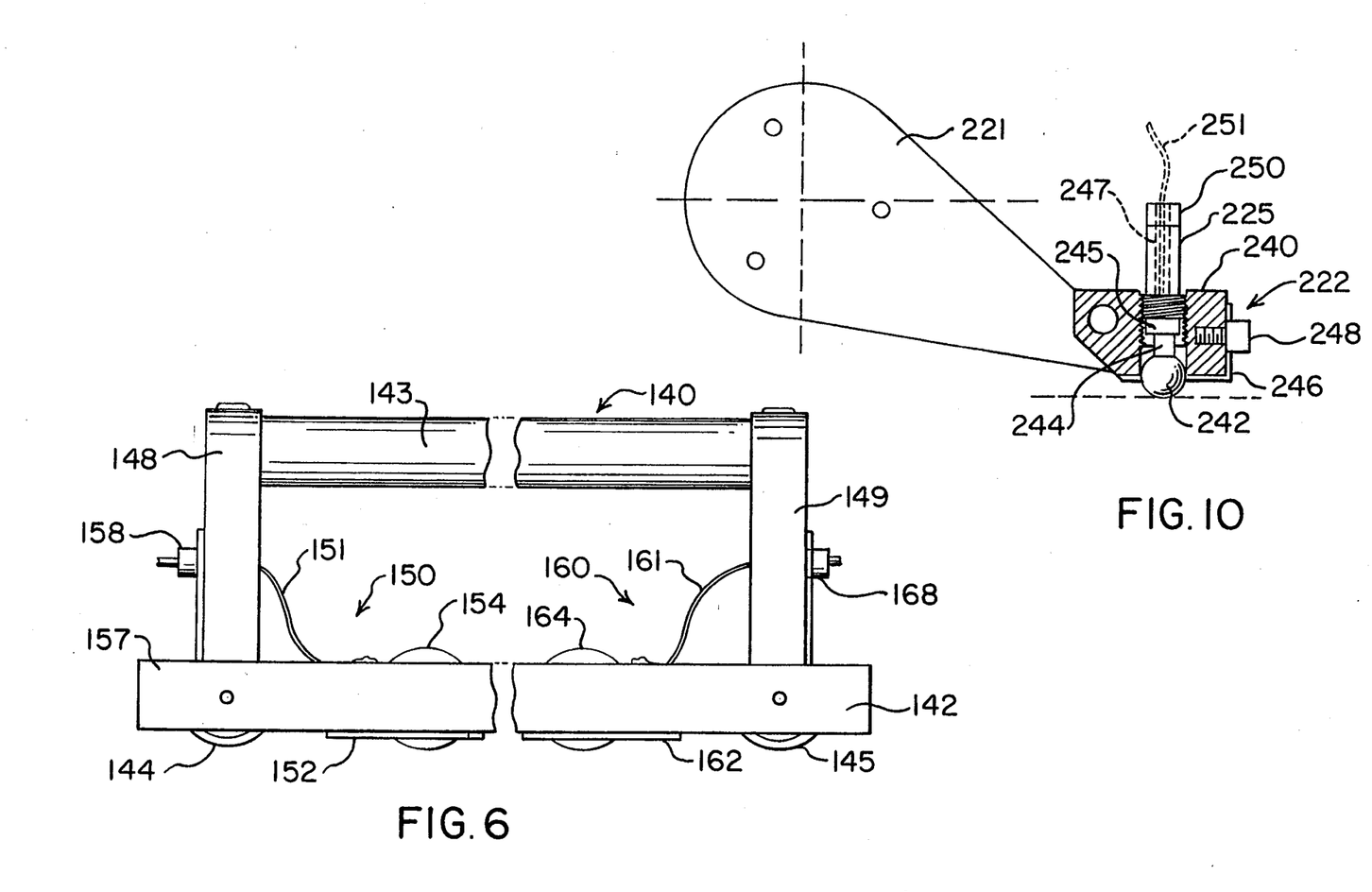
FIG. 6 is an alternate embodiment implemented with discrete transmitter and receiver components in a common carriage mount.
FIG. 10 is a partially sectioned view of the impact arm subassembly of the FIG. 9 impactor.

An alternate embodiment wherein identical transducer roller elements fabricated as replaceable modules and employed within a common frame, is shown as unit 140 in FIG. 6. As with the FIG. 1 embodiment, a generally rectangular frame 142 is used with quadrant located wheels, such as 144 and 145. Straps 148 and 149 attach handle 143 to frame 142 for manual movement of unit 140.

Crystal roller modules 150 and 160 are suspended from opposite ends of frame 142 preferably by the same flexible parallelogram structure described above. For module 150, housing 152 contains the mounting frame for crystal roller 154 with a flat spring and ball jointed link retaining housing 152 in position from a beam attached to end 157 of frame 142. The output cable 151 for module 150 is coupled to connector 158 for attachment to a remote device. Similar functions are provided by elements 161, 162, 164 and 168 for module 160.

Note that the break lines around the middle of carriage 140 are intended to suggest that the left and right portions of carriage 140 can either have a fixed relationship or can have an adjustment connection therebetween. For instance, slide rods and set screws, or worm gear coupler assemblies, could join the right and left halves of frame 142 and handle 143. This would allow precise control of the physical spacing between rollers 154 and 164.

In operation, unit 140 is moved with its wheels engaging the surface of the specimen under test. Its crystal rollers 154 and 164 each adjust to the irregularities of the surface they encounter independently of surface engagement by the carriage support wheels (e.g., wheels 144 and 145). The controller in communication with unit 140 introduces an actuating signal to one crystal to cause it to introduce an acoustic signal to the specimen. The other crystal remains passive, but will respond to acoustic signals reflected from within the test volume. It is preferable to pulse modulate the actuated crystal to prevent masking of reflected signals at the passive crystal.

The integrity of the material under test can only be determined by accurately measuring the time necessary for an acoustic signal to pass through or reflect from within such material. Therefore, it is necessary to apply this signal on a pulsed basis rather than on a continuous basis so as to set a definite start time for the measurement of the velocity of a signal through the mass.

Figure 7:
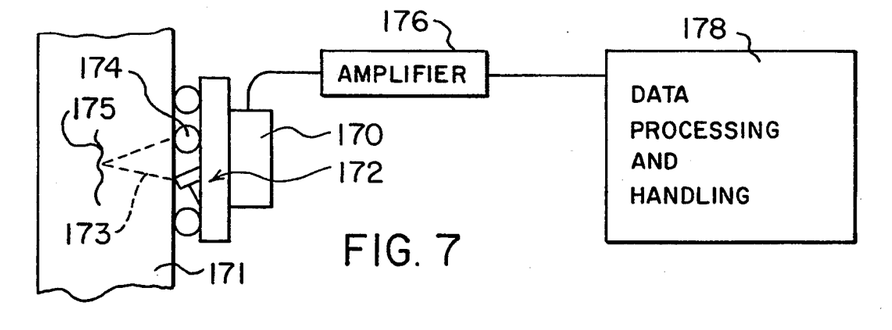
FIG. 7 illustrates an embodiment of a carriage containing both an impactor and a sensing roller operating in an impact echo mode.

FIG. 7 shows a carriage 170 adapted to perform Impact Echo internal surveying of a solid specimen 171. Carriage 170 contains an impactor 172 which introduces acoustic signal 173 into specimen 171 for echo detection by sensor roller 174. Preferably, the point of impact by the hammer element of 172 is as close as practical to detector roller 174 so as to minimize the angle of selected signals. Hammer 172 is preferably a rotary solenoid-actuated device along the lines of FIGS. 9 and 10 below. It is preferably actuated on a periodic basis each time carriage 170 is moved for a predetermined increment of travel. The actuating signal can originate from a mechanical linkage, as by a tachometer-type device, or by pulses originated by a controlling computer or the like.

Ordinarily, the impact pulses from hammer 172 will reflect from the far interior wall of specimen 171, thus indicating homogenous interior material. However, the time of travel of the acoustic echo is reduced when an interior flaw, such as 175, is encountered by the acoustic wave. The received signal from detector 174 is passed through an amplifier 176 before introduction to data handling and processing apparatus 178.

Figure 8:
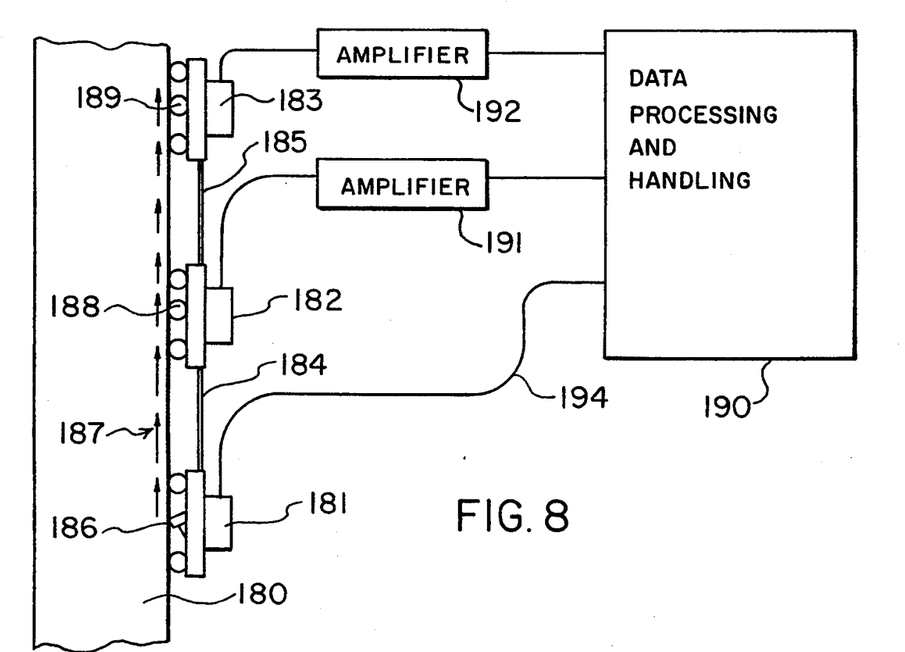
FIG. 8 is an arrangement of tandem carriages coupled for detecting shear waves.

An arrangement for sensing SASW or shear waves passing through a solid specimen 180 is presented in FIG. 8. Here carriages 181, 182 and 183 are interconnected by relatively fixed links 184 and 185, although links 184 and 185 might include pivotable ball joints or the like if desired. As shown, carriage 181 contains a hammer 186 which impacts the surface of specimen 180. This action produces both a P-wave and a shear wave (S-wave) with the latter indicated generally at 187.

As the S-wave 187 travels along in proximity to the surface of specimen 180, it first encounters sensing roller 188 and then roller 189 of carriages 182 and 183, respectively. The sequence of detected signals are thence coupled to the computer, or other data processing and handling components 190, via amplifiers 191 and 192. This produces an indication of flaws near the surface of specimen 180.

Note that hammer element 186 can receive actuation signals from computer 190 over cable 194, or could respond to a mechanism on carriage 181 to establish an impact after a given amount of travel of carriage 181. Preferably, the distance from hammer 186 to roller/sensor 188 is the same as the distance from roller 188 to roller 189. The chain of linked carriages can include additional units, if desired. Further, each unit can have it wheels and rollers configured for parallel movement of the entire assemblage of carriages. The latter has the advantage of surveying a wider area of the specimen 180 rather than the relatively narrow line associated with movement of the FIG. 8 array.

Figure 9:
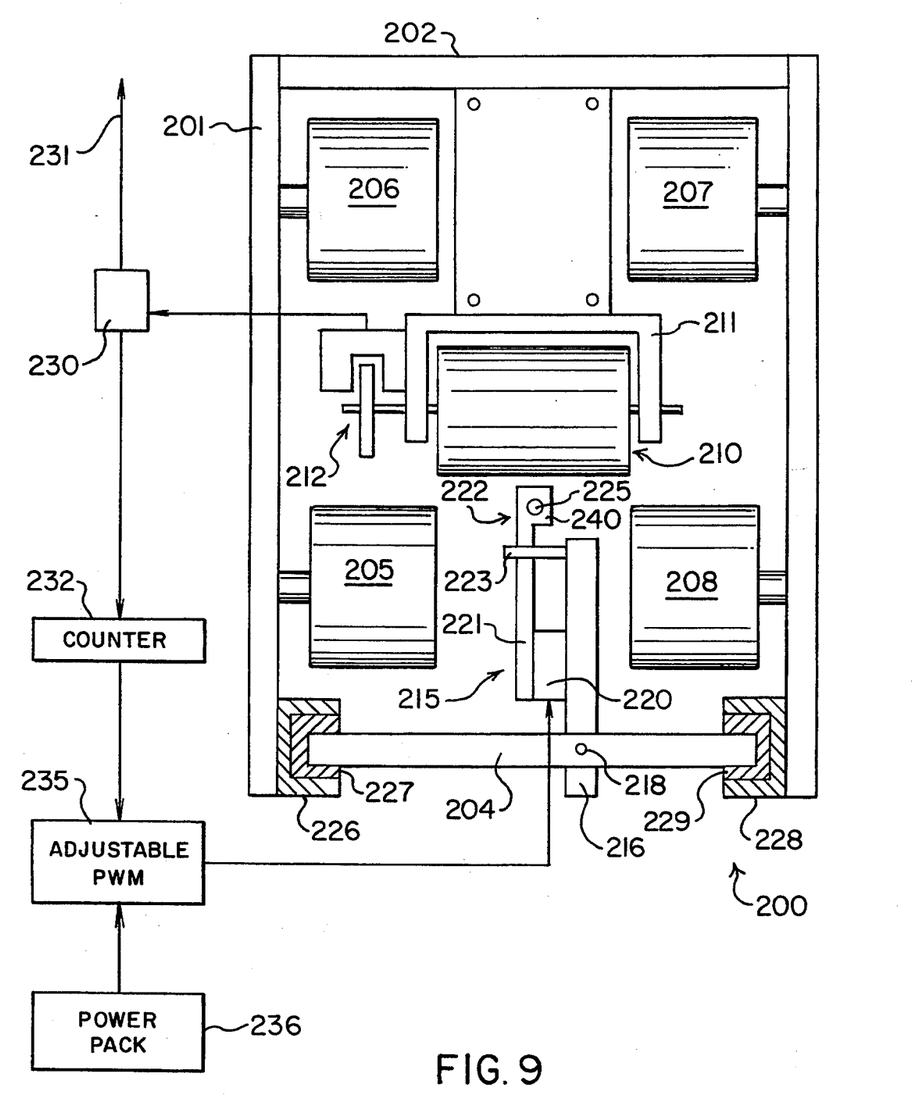
FIG. 9 is a carriage embodiment incorporating a rotary solenoid actuated impact element.

Another embodiment of the carriage and electrically actuated hammer is shown in FIGS. 9 and 10. Carriage 200 includes a surrounding frame arrangement formed by beams 201, 202, 203 and 204 which retain the specimen surface engaging wheels 205, 206, 207 and 208 in position. An acoustic transducer 210, with its flexible mounting subassembly 211 and tachometer mechanism 212, all are configured and operate substantially as described previously herein.

The specimen impacting function is accomplished for carriage 200 by an electrical solenoid assembly 215 attached to beam 204 via mounting plate 216. Plate 216 is held to beam 204 by a screw 218 in a manner which allows adjustment of assembly 215 towards or away from roller/detector 210. Once set, plate 216 is maintained in an extended but fixed relation to beam 204 by screw 218. It is preferable for echo sensing to maintain hammer assembly 222 as close to detector roller 210 as possible as mentioned for FIG. 7 above. For shear wave detection, greater separation between hammer 222 and detector 210 is preferred normally.

The body of rotary solenoid 220 is attached to plate 216 and has a pivotably mounted actuator arm 221 extending therefrom with impact head assembly 222 at the outer extremity of arm 221. Solenoid 220 normally spring biases arm 221 in an upward direction.

Thus, since the FIG. 9 view is looking downwardly, it is readily apparent that stub 223, which extends transversely from plate 216, is positioned to limit the upward travel of arm 221 as well as to dampen any oscillation of arm 221 when solenoid 220 is actuated. Impact head assembly 222 includes a force transducer 225 to produce an output signal corresponding to each specimen impact by the hammer.

Beam 204 is suspended between beams 201 and 203 by brackets 226 and 228 which have electrical insulator caps 227 and 229 respectively contained therein. This allows use of the outer shell of head assembly 222 to form part of the electrical contacts for force transducer 225, as is more apparent in the description below for FIG. 10.

Associated with carriage 200 is circuitry for automatically actuating solenoid 220. Each time tachometer 212 produces a pulse specifying that carriage 200 has moved a predetermined distance, this pulse is passed through splitter/isolator circuit 230 where it is passed to a remote device at output 231, and to the input for counter 232. Counter 232 is preferably selectable by the user to produce an output pulse and reset itself after the selected number of tachometer 212 pulses are coupled into counter 232.

Occurrence of the selected number of pulses causes counter 232 to introduce a pulse to adjustable pulse width modulator circuit 235. Circuit 235 responds to the counter 232 pulse by applying operating power from source 236 to actuate solenoid 220 for a predetermined length of time. Ideally, the width of the pulse from modulator 235 is adequate to cause head assembly 222 to approach the specimen surface, but not to stay engaged with that surface. Carriage 200 can accommodate mounting of all of the FIG. 9 circuitry if desired although that circuitry could reside in a belt or back pack on the user. Alternatively, that circuitry could reside in the remote data processing location.

Impactor head assembly 222 on the outer end of actuator arm 221 is shown in somewhat greater detail in FIG. 10. Block 240 of assembly 222 receives ball 242 in a cup-shaped end of collar 244 which is, in turn, axially aligned with piezoelectric crystal 245. Ball 242 is prevented from dropping out of block 240 by angle bracket 246 which is attached to block 240 by nut 248.

Force transducer assembly 225 includes plug 250 that is threaded to engage block 240 and the upper surface of crystal 245 so as to hold it in place. In addition, one electrode of crystal 245 passes coaxially through the center conduit 247 of plug 250 in electrical isolation from block 240 and the outer portion of plug 250. The other electrode of crystal 245 is in electrical communication with the outer portion of plug 250. As a result, attachment of a coaxial connector 251 to the upper end of plug 250 establishes an output lead for coupling impact designating signals to other equipment.

In operation, arm 221 is normally biased upward and away from the specimen surface by rotary solenoid 220. Introduction of an actuator pulse to solenoid 220 causes arm 221 to pivot clockwise, as seen in FIG. 10, until ball 242 strikes the specimen surface. A vertical force component is introduced through collar 244 to compress crystal 245 thereby causing it to produce an electrical output pulse coupled through cable 251 to a utilization device.

It is possible to configure the crystal elements of the roller for enhanced sensitivity to either P-waves or S-waves. The configuration of FIG. 4, for example, is better suited for sensing or creating compression or P-waves even though it can also work with S-wave generation and detection. Some examples of piezoelectric roller transducers especially structured for enhanced utility for shear or S-waves are shown in FIGS. 11, 12 and 13.

Figure 11:
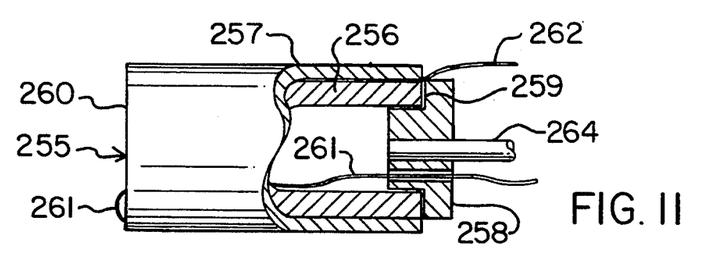
FIG. 11 is a partially sectioned view of a sensor roller configured for generating or responding to shear waves.

Roller 255 of FIG. 11, for example, includes cylindrical piezoelectric crystal 256 with a resilient outer coating 257 and a retaining end block or disk 258. Crystal 256 is fabricated with an orientation for greater sensitivity in its axial direction. It has washer-shaped electrodes on its end faces 259 and 260 to which are connected leads 261 and 262. Disk 258 is mounted relative to the carriage frame so as to allow rotary motion of roller 255 around shaft 264 as the assembly rolls over the specimen surface, but with this mounting further preventing any axial motion of end face 259 relative to the host carriage. However, end face 260 is free to move in an axial direction.

Accordingly, when an electrical signal is introduced to wires 261 and 262, crystal 256 will expand and contract in an axial direction so as to couple an acoustic signal into the specimen. When functioning as a receiver, the presence of S-waves on the specimen surface will cause axial force applications to roller 255 thereby producing electrical signals at output leads 261 and 262.

Figure 12:
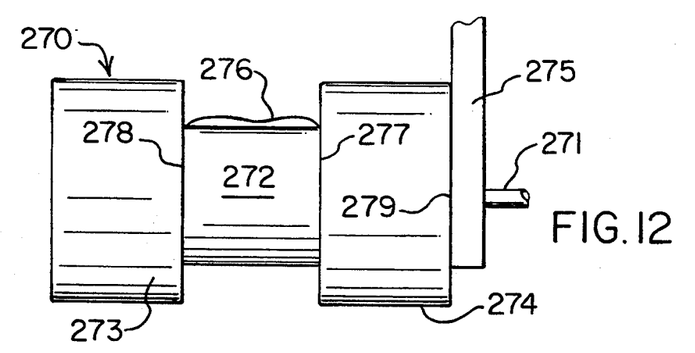
FIG. 12 is an alternative arrangement of a shear wave sensing or producing roller.
Figure 13:
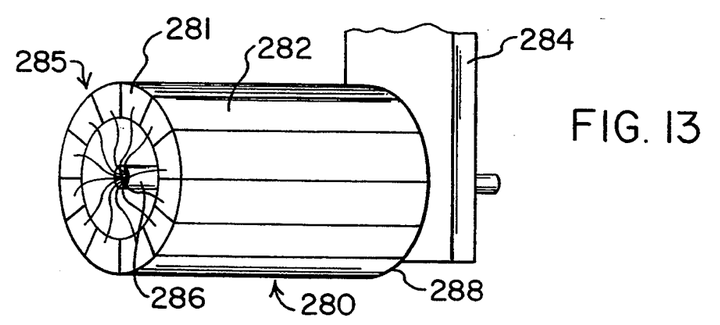
FIG. 13 is another configuration of piezoelectric crystal segments for shear wave usage.

In FIG. 12, roller assembly 270 sandwiches a hollow, or solid cylindrical piezoelectric crystal 272, between inert rollers 273 and 274 as a unit for rotation around shaft 271. A plate 275 allows this rotary motion but prevents any axial motion of face 279 between roller 277 and plate 275. Electrodes, such as 276, are attached to the end faces 277 and 278 of crystal roller 272 and brush coupled to produce output signals, as described previously herein. In this case, axial motion is transferred into or out of the specimen surface essentially by outer roller 273 which is free to move axially thus coupling axial forces into and out of crystal 272 while isolating crystal 272 from actual engagement of the specimen surface.

Figure 14:
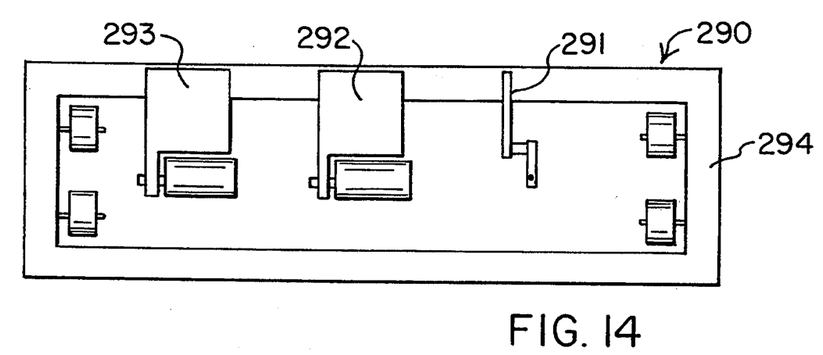
FIG. 14 is an alternate carriage arrangement especially configured for self-contained shear wave sensing and measuring transverse to the direction of motion of the carriage.

FIG. 14 is a roller assembly 280 structured from a series of bonded or otherwise retained segments of elongated crystal elements such as crystals 281 and 282. End face 285 has an electrical connection from each electrode introduced through axial tube 286 for passage through retainer plate 284 and coupling to detectors. Note that each segment end on the other end face 288 could likewise pass through a similar tube, although it is possible to use a single common plate with a common electrode for all detectors connected to the plurality of wires from the other end. In any event, roller 280 is allowed to move axially at face 285 but not at face 288 thereby permitting axial vibration exchanges with the specimen surfaces.

FIG. 14 is a somewhat idealized configuration of a carriage 290 with multiple modules 291, 292 and 293 arrayed within frame 294 for S-wave production and sensing. A rotary solenoid impactor module 291 operates, as described before, to introduce a shear wave into the specimen. Axially oriented sensor modules 292 and 293 are positioned so that the distance between their center points is about the same as the distance from the center point of roller 292 to the point of impact created by module 291.

As carriage 290 is moved vertically as viewed in FIG. 14, lines of S-wave measurements are made across the specimen surface. Of course, it is acceptable to employ a greater or lesser number of the sensor modules as well as to interchange them in their relative positions on frame 294.

The embodiments disclosed herein utilize four quadrantly located wheels for each carriage. However, it is readily apparent that a satisfactorily operable carriage is possible within the spirit of this invention with greater or lesser numbers of support elements of wheels, tractors or any suitable alternative.

While the exemplary preferred embodiments of the present invention are described herein with particularity, those having normal skill in the art will recognize various changes, modifications, additions and applications other than those specifically mentioned herein without departing from the spirit of this invention.

What is claimed is:

1. Apparatus for transporting acoustical testing mechanisms across the surface of a solid specimen for analyzing the quality of the interior of that specimen by acoustic waves traveling within said specimen and reflecting from surface boundaries within the specimen comprising an assembly for acoustically communicating with the specimen including roller means for rolling on the external surface of the specimen and an acoustically communicating element retained within said roller means, a frame, means attached to said frame for allowing movement in a direction of said frame over the surface of the specimen with a relatively constant spacing therefrom, and means attaching said assembly to said frame for engaging the specimen surface as said frame is motivated over the specimen surface for establishing acoustical communication with the interior of the specimen, said attaching means including means for permitting said assembly to move in a direction normal to the specimen surface and to move in a rotary motion relative to a line of the direction of movement of said frame over the specimen surface, said permitting means including a flat spring and a network of pivotably connected link elements arranged between said assembly and said frame with said flat spring oriented generally parallel to the specimen surface and forming a parallelogram perpendicular to the specimen surface in conjunction with said network of link elements for applying a force to said assembly for resiliently urging said assembly towards the specimen surface with at least two degrees of freedom relative to said frame whereby said assembly is retained in constant engagement with the specimen surface despite irregularities on the exterior of the specimen.

2. Apparatus in accordance with claim 1 wherein said acoustically communicating element includes a piezoelectric crystal formed as a cylinder with an axis thereof parallel to the specimen surface and transverse to the direction of movement of said frame.

3. Apparatus in accordance with claim 2 wherein said roller means includes an acoustically transmissive layer overlying said cylinder for providing a protective interface between said cylinder and the surface of the specimen.

4. Apparatus in accordance with claim 1 wherein said acoustically communicating assembly includes means for impacting the surface of the specimen.

5. Apparatus in accordance with claim 4 wherein said impacting means includes means responsive to movement of said frame for actuating said impacting means after a predetermined amount of movement has occurred between said frame and the specimen.

6. Apparatus in accordance with claim 5 wherein said means attached to said frame includes at least one wheel for engaging the specimen surface, said impacting means including a shaft, means mounting said shaft for movement in a direction normal to the surface of the specimen, and means coupling said wheel for causing said shaft to impact the specimen surface in response to movement of said wheel over the specimen surface for a predetermined distance.

7. Apparatus in accordance with claim 6 wherein said shaft mounting means includes a collar attached to said shaft and having a shoulder extending transverse to the length of said shaft, and said coupling means includes at least one bar extending from said wheel in parallel but offset relation to the rotational axis of said wheel for sequentially lifting and releasing said shoulder as said wheel moves over the specimen surface.

8. Apparatus in accordance with claim 7 wherein said shaft mounting means includes means biasing said shaft in a direction towards the specimen surface for applying impacting force to said shaft after the shaft is released by said bar.

9. Apparatus in accordance with claim 8 which includes a plurality of said impacting means attached to said frame.

10. Apparatus in accordance with claim 9 wherein shafts of said plurality of impacting means are released at different points of travel of said wheel over the specimen surface.

11. Apparatus in accordance with claim 5 which includes means sensing operation of said impacting means for producing a signal reflecting actuation of said impacting means.

12. Apparatus in accordance with claim 4 wherein said impacting means includes a solenoid means and means for selectively introducing an energizing signal to said solenoid means.

13. Apparatus in accordance with claim 1 wherein said acoustically communicating element includes means for detecting acoustic signals at the surface of the specimen, said apparatus further including means for injecting an acoustic signal into the surface of the specimen, and means mounting said injecting means on said frame in relatively fixed spatial relation to said acoustic signal detecting means.

14. Apparatus in accordance with claim 13 wherein said injecting means includes at least one mechanical element for impacting the surface of the specimen.

15. Apparatus in accordance with claim 14 wherein said roller means for rolling on the surface of the specimen includes piezoelectric crystal means for producing an electrical output signal in response to acoustic signals from the specimen at a location of engagement thereof by said roller means.

16. Apparatus in accordance with claim 13 wherein said detecting means includes piezoelectric crystal means for producing an electrical output signal in response to acoustic signals from the specimen at a location of engagement thereof by said roller means.

17. Apparatus in accordance with claim 16 wherein said injecting means includes a second roller means including piezoelectric crystal means responsive to an electrical signal thereto for producing acoustic signals for introduction into the specimen at the location of the engagement thereof by said second roller means.

* * * * *